United States Patent [19]

Carver

[11] 4,290,300

[45] Sep. 22, 1981

[54] SUCROSE DENSITY GRADIENT SYSTEM

[76] Inventor: Joseph Carver, 31 West Blvd., East Rockaway, N.Y. 11518

[21] Appl. No.: 952,283

[22] Filed: Oct. 18, 1978

[51] Int. Cl.³ .............................................. G01N 9/18
[52] U.S. Cl. ..................................... 73/32 R; 366/273
[58] Field of Search ................. 73/438, 32 R; 137/91; 252/315; 366/273

[56] References Cited

U.S. PATENT DOCUMENTS 3,060,130  10/1962  Sacks .............................. 73/32 R X Primary Examiner—Jerry W. Myracle

[57] ABSTRACT

An improved method for separating and immobilizing constituent cells of heterogeneous intact organic cells and the molecular components of organic cells into bands in a liquid gradient column which has sucrose, cesium chloride or other similar materials and also harvesting or removing said gradients, from their lower to upper or upper to lower deposits or portions.

9 Claims, 6 Drawing Figures

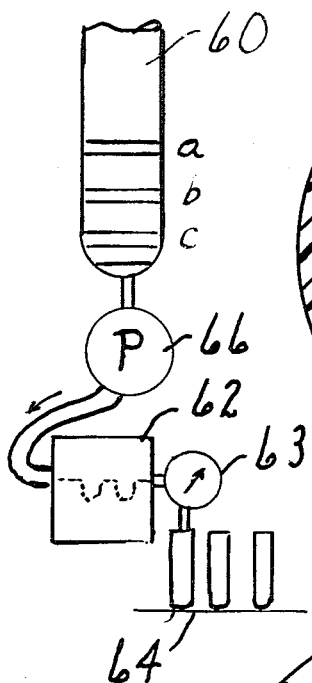
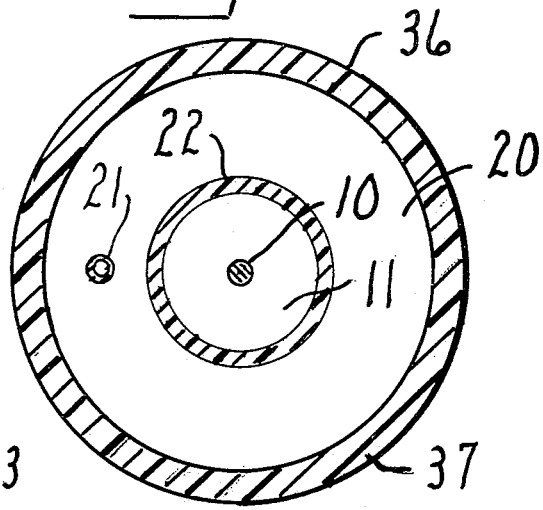
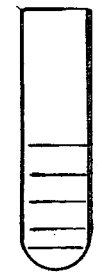
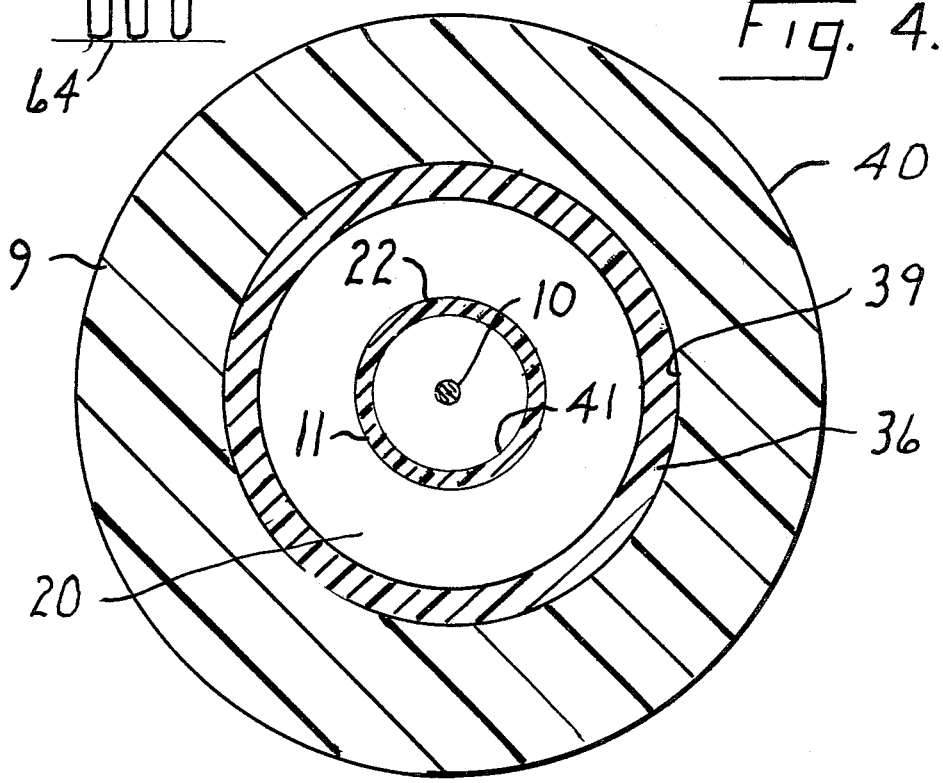

SUCROSE DENSITY GRADIENT SYSTEM

SUMMARY

Liquid columns having a gradient density are useful analytical implements which may be employed advantageously for the quick and convenient determination of the density or specific gravity of various materials. Such columns indicate the density or specific gravity of materials that are immersed in the column. Due to their floating in suspension, with equilibrium buoyancy in the column and finding a position in the column according to their specific gravity, the density of the liquid in the column and that of the immersed material will correspond.

A primary object of this invention is to provide an improved apparatus and method for both making and harvesting a sucrose or similar density gradient.

It is also an object of this invention to provide a linear or exponential column within a test tube in which the sucrose density gradient will find equilibrium somewhere throughout the gradient.

A still further object is to provide the linear or exponential column with means to locate the strata where the material has found its equilibrium.

Further objects of this invention shall be apparent by reference to the detailed description and the drawings.

DESCRIPTION OF THE DRAWINGS

FIG. 3 is a cross sectional view taken on line A—A of FIG. 1, FIG. 4 is a cross sectional view taken on line 4—4 of FIG. 1, FIG. 5 is an illustration of the sequence of operations in harvesting a density gradient; and FIG. 6 shows the separated gradients.

In making a sucrose, cesium chloride or other such material as well as the harvesting (the removal) of said gradients, it is important to note that the same apparatus is used for both making and harvesting with only slight modifications.

Figure 1:
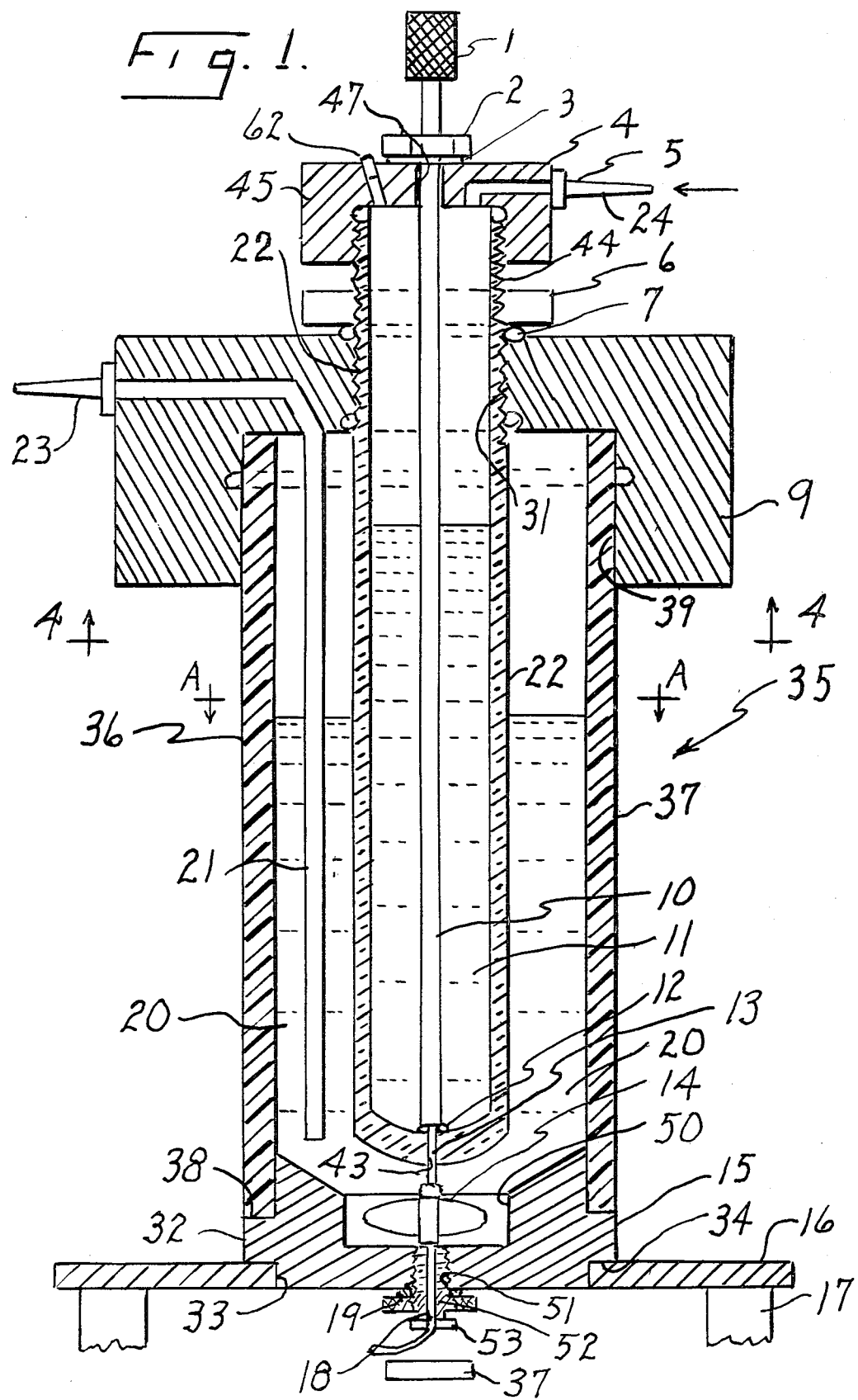
FIG. 1 is an elevational view of the apparatus for making a sucrose, cesium chloride.
Figure 2:
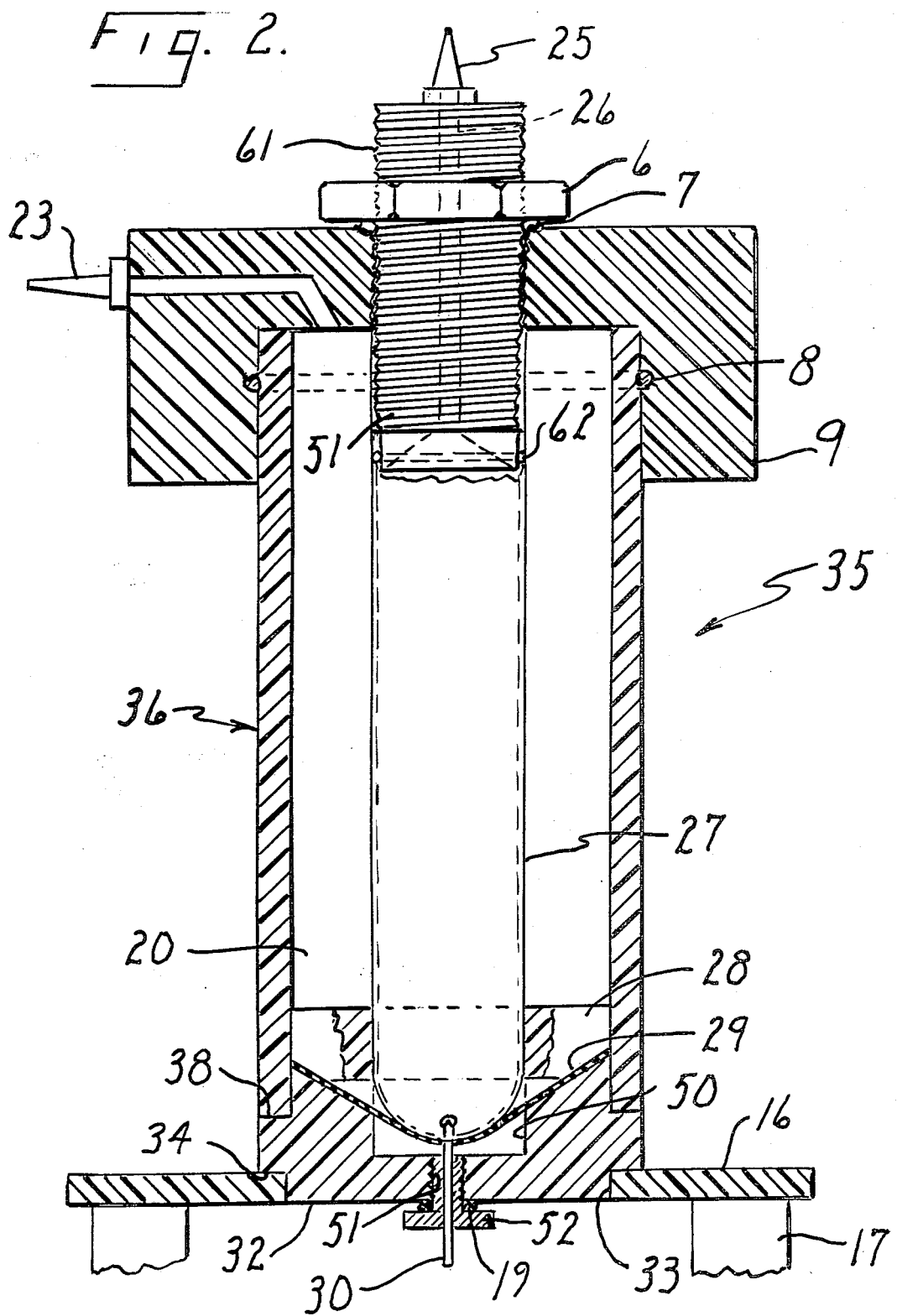
FIG. 2 is an elevational view of the apparatus for harvesting gradients.

Referring to FIG. 1 there is illustrated partially in cross section, a bench with legs 17 and top 16. The top 16 is cut out at its center to permit a circular base 32 to fit into the cutout portion 33 and rest upon the top 16 at 34. The apparatus 35 comprises a circular base 32 that supports a circular hollow body 36 and its components. The circular shaped body 36 at its base sits upon a shelf 38 of the base 32. The circular shaped body 36 supports a top 9, top 9 is provided with a circular cutout portion 39 that fits over and around the body 36, and the top portion 9 is provided with a circular cutout opening 31 through which a clear plastic tube 22 extends to provide an inner chamber 11. The circular shaped body 36 (FIG. 3) is provided with an acrylic wall 37 that provides a chamber 20 between the top 9 and the base 32 (FIGS. 1 & 2). The top 9 is provided with an inlet port 23 that extends to a tube 21 (FIG. 1). Tube 21 extends from top 9 to the bottom of the chamber 20. Inlet port 23 is used to pressurize or to vent chamber 20. A premeasured volume of heavy phase sucrose is introduced into outer chamber 20 through the top of the circular body 36 with top 9 removed.

Inner chamber 11 extends through the top 9 and is provided with a threaded top end 44. A top element 45 is threadably secured to the top end 44. Element 45 has two ports 24 and 62, port 24 permits charging light phase sucrose through it to be carried into the inner chamber 11 and also pressurizing inner chamber 11, port 62 is a vent port. Element 45 also has a central opening 47 through which a valve stem 10 extends from a knurled head 1 to the bottom of chamber 11 and is provided with a solid needle end 13 that extends through a port 43 and is provided with an "O" ring 12 for sealing between the valve stem and the tube 22.

Base 32 is provided with a central cutout portion 50 and the area 50 is provided with a port 51 that is threaded to permit mounting and sealing with a gasket 19, a threaded plug 52. Plug 52 is bored through its center to permit the tube 18 to pass through. A magnetic stirrer 37 is provided to be positioned externally under tube 18. The magnetic stirrer 37 is placed under the area 50 and provides one means (using A magnetic stirrer bar 14) to stir the sucrose when the light phase is drawn through port 43, when valve stem 10 is raised opening port 43 to outer chamber 20. Thus mixing the light phase sucrose with the heavy phase sucrose. An alternate method of mixing the light phase sucrose with the heavy phase sucrose in and around the area of 50 is to bubble air or an inert gas into inlet port 23 through tube 21 to the bottom of chamber 20. The mixed sucrose will drain out through the stem tube 18. Thus the sucrose, cesium chloride gradient is produced.

When port 23 of outer chamber 20 is left vented to atmosphere and when vent port 62 of inner chamber 11 is sealed to atmosphere, the result is a greater volume of heavy sucrose mixed with the lesser volume of light phase sucrose thereby producing an exponential sucrose gradient. If on the other hand port 23 is vented to atmosphere and port 62 is sealed while at the same time pressurized air or inert gas is introduced into inner chamber 11 through port 24 thereby causing a greater volume of light phase sucrose in chamber 11 to be forced through port 43 and mix with heavy phase sucrose in outer chamber 20 thus producing an exponential gradient (the reverse curve) of the previously described exponential gradient. If both ports 23 and 24 are vented to atmosphere a lineal gradient is produced.

Referring to FIG. 2 there is illustrated a similar apparatus to that shown in FIG. 1 with some modifications. The base 32, supported by bench 17 retains the apparatus 35 in which the same circular body 36 rests on base 32 and the same cap 9 with "O" ring seal 8 rests on the top of body 36, but tube 21 is removed, together with tube 22 and needle valve 10 is removed as well as top element 45. A centrifuge gradient tube 27 (which has been previously filled with formed gradient and layered with biological material to be separated and has already been high speed centrifuged, now has at the upper end an inner core 51 with "O" ring seal 62 placed into it. At the lower end of tube 27 there is a tube bushing guide 28 mounted in chamber containing thin flexible rubber sheet as a gasket 29, its bottom surface rests upon the base 32 in chamber 20. Entire tube assemblies 27 and 61 have previously been threaded into cap 9 and locked with nut 6. This is placed into chamber 20 with bottom of tube 27 passing through the guide bushing 28 and is forced down over tip of needle 30 thus puncturing rubber gasket 29 as well as tube 27. It is important to make sure that the piercing is accomplished by the downward thrust of the entire assembly. At this point with port 25 at the upper end of tube 27, vented to atmosphere, the gradient can be metered and pumped through outlet port 30. This allows for removal of the gradient from the bottom (heavy phase sucrose) to the top (light phase) or a heavy concentration of sucrose may be pumped into needle out port 30 thereby forcing the entire formed gradient with separated bands (components) to be forced out of insert 51 via center bore 26 and out port 25 to collecting test tube. This method allows the light phase of the formed sucrose gradient to be harvested first followed by the heavier phase. It may be passed through a "UV" monitor or other such similar instrument and ultimately collected into many different fractions as shown in FIG. 5. FIG. 5 shows schematically the method of connecting the test tube 60 having the separated portion, connected to a Peristaltic pump 66 and the pump outlet connected to an ultra-violet monitor 62. The monitor 62 is provided with a recorder 63 graphically illustrating the gradient in flow through the UV monitor of the separated components enroute to test tubes 64.

The device as described is for the harvesting of a gradient working from the heavy phase to the light phase or vice versa as shown in FIG. 6.

The invention described in detail in the foregoing specification is subject to changes and modifications without departing from the principle and spirit thereof. The terminoloy used is for purposes of description and not of limitation; the scope of the invention being defined in the claims.

What is claimed is:

1. In a device for preparing an exponential or linear sucrose or similar type gradient liquid column within a test tube or centrifuge tube, having two chambers concentric one within the other, each of which may be pressurized or vented to atmosphere, an outer chamber provided with a mixing bar, an inner chamber provided with a valve stem, both chambers permitting a variable volume charge, to form a light concentration sucrose in one chamber and a heavy concentration sucrose in the other chamber, to provide a linear gradient as a liquid column within the test tube, with the linear or exponential gradient formed, the introduction of a biological material sample containing one or more components of varying molecular weight or size to be layered atop the formed gradients to be used for quick and convenient determination of the density or specific gravity or the molecular size and weight of the various biological components, due to the distribution of the biological components over the sucrose or linear exponential gradient as they find a position in the liquid column and deposit upon the layered sucrose or float in stratified suspension through the gradient.

2. In a device according to claim 1 in which there are linear gradients formed when the entire system is open to atmosphere.

3. In a device according to claim 1 in which there are exponential gradients formed when, one of the chambers is sealed and pressurized to allow a greater volume of a particular phase sucrose to mix with the normal unpressurized phase sucrose to produce an "off" linear or exponential gradient.

4. In a device according to claim 1 in which a cap is provided to seal the outer chamber from the inner chamber and atmosphere, and a vent provided to atmosphere that may be opened or closed.

5. In a device according to claim 1 in which a cap is provided with a seal for the inner chamber and provided with ports for charging and venting or pressurizing the inner chamber.

6. In a device according to claim 1 in which a stem valve is mounted in the inner chamber to provide a seal, said valve movable to open and close the inner chamber, the base of inner chamber provided with an outlet for draining contents.

7. A method of harvesting a linear or exponential sucrose density gradient, containing a biological sample whose several components after having been centrifuged (ultra speed) have found equilibrium and have stratified themselves, through the sucrose density gradient, according to their specific gravities, molecular weight and size and with the component parts separated, piercing said test tube and withdrawing by means of a peristaltic pump and tubular needle inserted into the test tube, the sucrose at the density gradient at which it has settled, and by means of an ultra-violet monitor scanning both the Non-UV absorbing sucrose density gradient and the separated component biological bands (U.V. absorbing) as they are removed and by means of a recorder determining the optical density (O.D.) and concentration of each component band and depositing each of these bands sequentially into a test tube.

8. In a device for preparing an exponential sucrose or similar type gradient liquid column within a test tube or centrifuge tube having two chambers concentrically one within the other, the outer chamber provided with a vent port sealed for pressurizing, a magnetic stir bar provided for mixing, an outlet also provided, the inner chamber provided with a charging port and a vent port which may be sealed to permit pressurizing, also providing a sealed stem valve within the inner chamber.

9. A device for removing or harvesting centrifuge, stratified gradient which comprises an outer chamber and an inner chamber comprised of a centrifuge tube which forms an inner chamber which is in turn provided with a sealed aligning, vertically adjustable insert, said inner chamber provided with a port to be opened or closed, a guide bushing to align said inner chamber, said guide bushing provided with a gasket to seal said inner chamber, said gasket punctured in harvesting operation, said outer chamber provided with a piercing needle located below the inner chamber.

* * * * *